US009447009B2

(12) United States Patent
Belliere-Baca et al.

(10) Patent No.: US 9,447,009 B2
(45) Date of Patent: *Sep. 20, 2016

(54) METHOD FOR PREPARING ACROLEIN FROM GLYCEROL OR GLYCERINE

(71) Applicants: ADISSEO FRANCE S.A.S, Antony (FR); CENTRE NATIONAL DE LA RECHERCHE SCIENTIFIQUE, Paris (FR)

(72) Inventors: Virginie Belliere-Baca, Andresy (FR); Stephane Loridant, Meyzieu (FR); Jean-Marc Millet, Lyons (FR); Pascaline Lauriol-Garbey, Lyons (FR)

(73) Assignees: ADISSEO FRANCE S.A.S., Antony (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/010,724

(22) Filed: Aug. 27, 2013

(65) Prior Publication Data

US 2014/0171676 A1 Jun. 19, 2014

Related U.S. Application Data

(63) Continuation of application No. 13/140,109, filed as application No. PCT/FR2009/052577 on Dec. 16, 2009, now abandoned.

(30) Foreign Application Priority Data

Dec. 16, 2008 (FR) ...................... 08 58624

(51) Int. Cl.
| C07C 45/66 | (2006.01) |
| C07C 319/18 | (2006.01) |
| B01J 23/20 | (2006.01) |
| B01J 23/92 | (2006.01) |
| B01J 38/12 | (2006.01) |
| C07C 45/52 | (2006.01) |

(52) U.S. Cl.
CPC ............... *C07C 45/66* (2013.01); *B01J 23/20* (2013.01); *B01J 23/92* (2013.01); *B01J 38/12* (2013.01); *C07C 45/52* (2013.01); *C07C 319/18* (2013.01); *Y02P 20/584* (2015.11)

(58) Field of Classification Search
CPC ..... C07C 45/66; C07C 319/18; C07C 45/52; B01J 38/12; B01J 23/20; B01J 23/92; Y02P 20/584
USPC ....................... 558/308, 315, 345
See application file for complete search history.

(56) References Cited

U.S. PATENT DOCUMENTS

| 7,790,934 B2 | 9/2010 | Redlingshofer et al. |
| 7,846,861 B2 | 12/2010 | Redlingshofer et al. |
| 8,076,509 B2 | 12/2011 | Kasuga et al. |
| 9,079,841 B2 | 7/2015 | Lauriol-Garbey et al. |
| 2008/0183013 A1 | 7/2008 | Dubois et al. |
| 2008/0214384 A1* | 9/2008 | Redlingshofer et al. ....... 502/41 |
| 2010/0010260 A1 | 1/2010 | Kasunga |
| 2010/0247407 A1 | 9/2010 | Larcher |
| 2010/0247411 A1 | 9/2010 | Larcher |
| 2011/0112330 A1 | 5/2011 | Magatani et al. |
| 2011/0160491 A1 | 6/2011 | Dubois et al. |
| 2011/0288323 A1 | 11/2011 | Belliere-Baca et al. |
| 2012/0330049 A1 | 12/2012 | Paul et al. |

FOREIGN PATENT DOCUMENTS

| DE | WO 2006087083 A2 * | 8/2006 | ............. C07C 45/52 |
| FR | 2907444 A1 | 4/2008 | |
| FR | 2907445 A1 | 4/2008 | |
| FR | 2920767 A1 | 3/2009 | |
| FR | 2938535 A1 | 5/2010 | |
| WO | 2006087083 A2 | 8/2006 | |
| WO | 2006087084 A2 | 8/2006 | |
| WO | 2007058221 A1 | 5/2007 | |
| WO | 2007132926 A1 | 11/2007 | |
| WO | 2008006977 A1 | 1/2008 | |
| WO | 2008066079 A1 | 6/2008 | |
| WO | 2009127889 A1 | 10/2009 | |

OTHER PUBLICATIONS

Lauriol-Garbey et al. "New efficient and long life catalyst for gas-phase glycerol dehydration to acrolein" Journal of Catalysis 281 (2011) 362-370, published Jun. 23, 2011.*
Lauriol-Garbey et al. "Acid—base properties of niobium-zirconium mixed oxide catalysts for glycerol dehydration by calorimetric and catalytic investigation" Applied Catalysis B Environmental 2011, 106, 94-102, published May 17, 2011.*
Chai et al. "Sustainable production of acrolein: Gas-phase dehydration of glycerol over Nb2O5 catalyst" Journal of Catalysis 2007, 250, 342-349, published Aug. 6, 2007.*

(Continued)

*Primary Examiner* — Nyeemah A Grazier
*Assistant Examiner* — Amanda L Aguirre
(74) *Attorney, Agent, or Firm* — Cantor Colburn LLP (57) ABSTRACT

A method of preparing acrolein from glycerol or glycerine is disclosed. The method includes dehydrating glycerol or glycerine in the presence of a catalyst consisting of at least (a) a mixed oxide of zirconium and at least one metal, said metal being selected from niobium, tantalum and vanadium, or (b) a zirconium oxide and at least one metal oxide, the metal being selected from niobium, tantalum and vanadium, or (c) a silicon oxide and a mixed oxide of zirconium and at least one metal, the metal being selected from tungsten, cerium, manganese, niobium, tantalum, titanium, vanadium and silicon, or (d) a titanium oxide and a mixed oxide of zirconium and at least one metal, said metal being selected from tungsten, cerium, manganese, niobium, tantalum, titanium, vanadium and silicon.

14 Claims, 4 Drawing Sheets

(56) References Cited

OTHER PUBLICATIONS

Ulgen et al. "Conversion of Glycerol to Acrolein in the Presence of WO3/ZrO2 Catalysts" Catal. Lett. 2009, 131, 122-126.*

Haber et al. "Manual of Methods and Procedures for Catalyst Characterization" Pure & Appl. Chem. 1995, 67, 1257-1306.*

Atia, et al. "Dehydration of glycerol in gas phase using heteropolyacid catalysts as active compounds", Journal of Catalysis, Academic, Aug. 15, 2008, pp. 71-82, vol. 258, No. 1, Academic Press, Duluth, MN USA.

Chai et al.; "Sustainable production of acrolein: gs-phase dehydration of glycerol over 12-tungstophosphoric acid supported on ZrO2 and SiO2"; Green Chem.; 10; pp. 1087-1093; (2008).

Kleitz, et al. "Cubic 1a3d large mesoporous silica: synthesis and replication to platinum nanowires, carbon nanorods and carbon nanotubes", The Royal Society of Chemistry, ChemComm, pp. 2136-2137, Cambridge UK, (2003).

Kostova, et al. "Hexagonal mesoporous silicas with and without Zr as supports for HDS catalysts", Catalysis Today, pp. 217-223, vol. 65., (2001).

Ning, et al. "Glycerol Dehydration to Acrolein over Activated Carbon-Supported Silicotungstic Acids", Chinese Journal of Catalysis, pp. 212-214, vol. 29, No. 3., (2008).

Pagliaro, et al. "The Future of Glycerol: New Uses of a Versatile Raw Material: Dehydration", RSC Green Chemistry Book Series, pp. 54-64, Chapter 5, 2008).

PCT/FR2010/052855_Written Opinion , International Application Filing Date: Dec. 21, 2010; Date of Mailing Jan. 8, 2012, 6 pages; translation.

Tsukuda et al. "Production of acrolein from glycerol over silica-supported heteropoly acids", Catalysis Communications 8, pp. 1349-1353, (2007).

Zhao et al. "Triblock Copolymer Syntheses of Mesoporous Silica with Periodic 50 to 300 Angstrom Pores", Science, 1998, pp. 548-552, vol. 279, downloaded from www.sciencemag.org; May 17, 2012, DOI: 10.1126/ science.279.5350.548.

Katryniok et al; "A long-life catalyst for glycerol dehydration to acrolein"; Green Chem.; 12; pp. 1922-1925; (2010).

Gutierrez, et al. "Mo and NiMo catalysts supported on SBA-15 modified by grafted ZrO2 species: Synthesis, characterized and evaluation in 4,6-dimethyldibenzothiophene hydrodesulfurization", Journal of Catalysis, pp. 140-153, vol. 249, Elsevier Inc.,(2007).

JP2007268363 A, Oct. 18, 2007, Abstract Only, 1 page.

JP2008266165 A, Nov. 6, 2008, Abstract Only, 1 page.

Kantcheva et al., "Characterization of Zr6Nb2O17 synthesized by a peroxo route as a novel solid acid", Catalysis Communications (2008), 9(5), p. 874-879.

Nahas et al., "On the mechanism of zirconia textural stabilization by siliceous species during digestion under basic conditions", Journal of Catalysis, vol. 247, Issue I, Apr. 1, 2007, pp. 51-60, Abstract Only, 1 page.

M. Pagliaro et al., Angew. Chem. Int. Ed., 2007, 46, pp. 4434-4440, Abstract Only, 1 page.

International Search Report for International Application No. PCT/FR2009/052577; International Application Filing Date Dec. 16, 2009; Date of Mailing Jan. 9, 2010, English Translation, 3 pages.

Chai et al. "Sustainable production of acrolein: Preparation and characterization of zirconia-supported 12-tungstophosphoric acid catalyst for gas-phase dehydration of glycerol", Applied Catalysis A: General, 2009, pp. 213-222, vol. 353, Else.

International Search Report for International Application No. PCT/FR2011/051375, Application Filing Date Jun. 16, 2011, Date of Mailing Oct. 12, 2011, 4 pages; non-English.

Written Opinion for International Application No. PCT/FR2011/051375, Application Filing Date Jun. 16, 2011, Date of Mailing Oct. 12, 2011, 4 pages, English Translation.

\* cited by examiner

FIGURE 1

Glycerol conversion on catalyst A (□), B (△), C (◊) or D (○)
Acrolein selectivity on catalyst A (■), B (▲), C (♦) or D (●)

FIGURE 2

Hours

(△)   Glycerol conversion with fresh catalyst
(▲)   Glycerol conversion with regenerated catalyst
(□)   Acrolein selectivity with fresh catalyst
(■)   Acrolein selectivity with regenerated catalyst

FIGURE 3

Glycerol conversion into glycerol with catalyst A' (♦), D (●) or C (△)
Acrolein selectivity with catalyst A' (■), D (x) or C (▲)

FIGURE 4

Hours (△) Glycerol conversion with fresh catalyst
(▲) Glycerol conversion with regenerated catalyst
(□) Acrolein selectivity with fresh catalyst
(■) Acrolein selectivity with regenerated catalyst

METHOD FOR PREPARING ACROLEIN FROM GLYCEROL OR GLYCERINE

CROSS REFERENCED TO RELATED APPLICATIONS

This application is a continuation of U.S. application Ser. No. 13/140,109 filed on Aug. 9, 2011 as the U.S. National Phase of PCT International Patent Application No. PCT/FR2009/052577 filed Dec. 16, 2009, which claims priority to French Patent Application No. 0858624 filed Dec. 16, 2008, all of these applications are herein incorporated by reference in their entirety.

TECHNICAL FIELD

The present invention relates to a catalytic method for making acrolein by dehydration of glycerol or glycerine and to the application of such a method.

BACKGROUND

By glycerol is meant a glycerol either purified or not, preferably stemming from biomass and notably a highly purified or partly purified glycerol. A purified glycerol has a purity greater than or equal to 98%, obtained by distillation of glycerine. A non-purified or only partly purified glycerol may be in solution in methanol when it for example stems from transesterification of triglycerides, as described hereafter. By glycerine is notably meant glycerine of natural origin, stemming from hydrolysis of vegetable oils and/or animal fats, or more or less purified or refined or else raw glycerine of synthetic origin stemming from petroleum. As an example, raw glycerine has a titer comprised between 80 and 85%. Thus, subsequently in the description, reference is mainly made to the conversion of a glycerol or a glycerine stemming from biomass, but the invention of course is not limited thereto and its benefit extends to all glycerols and glycerines, regardless of their origins and their degrees of purity.

Gradual exhaustion of fossil energies leads industrials to envision the use of renewable raw materials stemming from the biomass for producing fuels. In this context, biodiesel is a fuel produced from vegetable or animal oil.

This product benefits from a green aura because of a clearly favorable $CO_2$ balance as compared with fossil energies. Diester® (or MEVOs, Methyl Esters of Vegetable Oils) is a biodiesel made by transesterification of triglycerides present in oleaginous liquids, notably palm, rapeseed and sunflower vegetable oils, by methanol. This transesterification co-produces approximately and according to the contemplated methods, 100 kg of glycerol per metric ton of diester®. The non-lipid portion of the raw material used, the cakes, is mainly exploited in animal feed.

This biodiesel is used, mixed with diesel oil. European Directives 2001/77/EC and 2003/30/EC, which will be applied in the near future, plan to introduce 7% in 2010 and 10% by the year 2015 of diester® in diesel oils. This substantial increase in the produced amount of biodiesel will generate significant amounts of glycerol equivalent to several hundreds of thousands of tons/year.

Some 1500 uses of glycerol have already been listed, among which the following illustrate its presence in many and various formulations, as examples:

moisteners in pharmacy (in suppositories and syrups) or in cosmetology in moisturizing creams, glycerine soaps, toothpastes, solvents in the food industry,
plasticizers or lubricants in the chemical industry.

These applications will prove to be clearly insufficient for absorbing the amounts of glycerol which will be co-produced with biodiesels and although in progress, the conventional glycerol market (soaps, pharmacy, . . . ) will not be able either to absorb such a surplus. It is therefore vital to find new applications with which the value of very large volumes of glycerol may be increased.

In view of this, many outlets have been investigated these recent years (see M. Pagliaro et al, *Angew. Chem. Int. Ed.* (2007) 46, 4434-4440 as well as M. Pagliaro, M Rossi: The Future of Glycerol, RSC Publishing, Cambridge (2008)), with in particular the six following routes for adding value thereto:

conversion into 1,3-propanediol and into 1,2-propanediol, notably used as base monomers in the synthesis of polyesters and polyurethanes, conversion into monoesters for the chemistry of lubricants, conversion into polyglycerols used as emulsifiers, food additives, conversion into acrolein (by dehydration) and into acrylic acid (by dehydration and oxidation), direct addition of value as additives for animal feed.

Acrolein and acrylic acid are traditionally used by controlled oxidation in the gas phase of propylene by oxygen from air in the presence of catalysts based on molybdenum and/or bismuth oxides. The thereby obtained acrolein may either be directly integrated into a two-step method for producing acrylic acid, or be used as a synthesis intermediate. The production of both of these monomers is therefore closely related to propylene which in substance is produced by steam cracking or catalytic cracking of petroleum cuts.

The markets of acrolein, one of the simplest unsaturated aldehydes, and of acrylic acid are gigantic since these monomers enter the composition of many mass marketed products.

Moreover, acrolein, a highly reactive compound because of its structure, finds many applications, notably as a synthesis intermediate. It is most particularly used as a key intermediate entering the synthesis of D,L-methionine and of its hydroxyl-analog derivative, 2-hydroxy-4-methylthiobutanoic acid (HMTBA). These food additives are massively used since they enter the composition of food supplements indispensable to the growth of animals (poultry, pigs, ruminants, fish, . . . ). In a certain number of cases, it may be profitable to be able to increase, or even ensure production capacities of existing industrial units by diversifying the engaged raw material. It therefore appears to be most particularly of interest to be able to increase acrolein productivity, while reducing the dependency towards this resource stemming from petroleum which is propylene.

BRIEF SUMMARY

The invention lies in the application of robust, active, selective and regenerable catalysts, with which acrolein may be directly produced from glycerol or glycerine, notably stemming from the biomass, according to the reaction:

With this alternative it is thus possible to have a competitive method for synthesizing acrolein, non-dependent on the propylene petroleum resource from another renewable raw material.

This possibility is particularly advantageous for synthesizing methionine or its analogs, such as its hydroxyl-analog (HMTBA) directly from the biomass.

Thus, the invention further relates to an application of this reaction to the synthesis of 3-(methylthio)propionic aldehyde (MMP), 2-hydroxy-4-methylthiobutyronitrile (HMTBN), methionine and its analogs such as 2-hydroxy-4-methylthiobutanoic acid (HMTBA), esters of HMTBA such as the isopropyl ester, 2-oxo-4-methylthiobutanoic acid, from acrolein.

Methionine, HMTBA and the esters of the latter and analogs are used in animal nutrition and in their industrial synthesis processes, acrolein is generally obtained by oxidation of propylene and/or of propane. Oxidation of propylene into acrolein by air in the presence of water is partial, and the resulting raw product, based on acrolein, also contains unreacted propylene and propane, water and by-products of the oxidation reaction, notably acids, aldehydes and alcohols.

Glycerol (also called glycerine) has been known for a long time as a source of acrolein (thermal transformation), it is a product which is widely found in nature, in the form of esters (triglycerides), in particular in all animal or vegetable oils and fats, which makes it a starting reagent available in sufficient quantity and in this respect may be used in industry. Actually, it is known that glycerol decomposes and gives acrolein when it is brought to temperatures above 280° C. This weakly selective reaction is accompanied by the formation of many by-products including acetaldehyde, hydroxyacetone, in addition to total oxidation products, CO, $CO_2$. It is therefore indispensable to control the reaction for transforming glycerol into acrolein in order to avoid unnecessary wasting of this resource and to do without a subsequent separation which is costly in energy with a complex acrolein purification process. Moreover, these impurities, mainly the aromatic derivatives are often at the origin of coke formation at the surface of the catalyst which poisons the latter over time; it is often necessary to regenerate the catalyst so as to again find satisfactory catalytic activity.

Many academic and industrial researchers have studied this reaction. The use of supercritical water as a reaction medium was notably contemplated. The use of a supercritical solvent on an industrial scale remains difficult for a continuous process because of particularly heavy infrastructures which require autoclaves operating under a very high pressure. On the other hand, the setting up of a continuous or batch process may be contemplated if a performing, selective and robust catalytic system is identified.

With view to the increasing interests for this chemical alternative, the literature mentions a great number of studies relating to the use of catalytic systems based on supported phosphor- or silico-tungstic heteropolyacids, mixed oxides and zeolites which may be used for continuous or batch processes in the liquid or gas phase.

Thus, documents WO-A-2006087083 and WO-A-2006087084 describe a method for catalytic dehydration of glycerol into acrolein in the gas phase, in the presence of molecular oxygen and of a strongly acid catalyst selected from zeolites, Nafion®, oxides of metals selected from aluminium, zirconium, titanium, niobium, tantalum, silicon, impregnated with acid functions in the form of sulfate, borate, tungstate, silicate and phosphate groups.

Document WO-A-2007132926 discloses a method for converting glycerol into acrolein in the presence of a catalyst selected from acid crystalline metallosilicates such as zeolites of the MFI or BEA structural type, comprising silicon and an element preferably selected from Al, Fe and Ga.

As compared with known methods, according to the described invention, a method is provided for preparing acrolein from glycerol or glycerine, by catalytic dehydration of glycerol in the presence of a catalyst which, while allowing conversion of the totality of the initial glycerol, may both be very easy to regenerate and has a long lifetime. The authors of the invention discovered that this catalyst was based on zirconium oxide and comprised at least:

a) a mixed oxide of zirconium and of at least one metal M, said metal being selected from niobium, tantalum and vanadium b) an oxide of zirconium and of at least one metal M, said metal being selected from niobium, tantalum and vanadium, c) a silicon oxide and a mixed oxide of zirconium and of at least one metal M, said metal being selected from tungsten, cerium, manganese, niobium, titanium, vanadium and silicon, d) a silicon oxide and a mixed oxide of zirconium and of at least one metal M, said metal being selected from tungsten, cerium, manganese, niobium, tantalum, vanadium and titanium, e) a titanium oxide and a mixed oxide of zirconium and of at least one metal M, said metal being selected from tungsten, cerium, manganese, niobium, tantalum, titanium, vanadium and silicon.

f) a titanium oxide and a mixed oxide of zirconium and of at least one metal M, said metal being selected from tungsten, cerium, manganese, niobium, tantalum, titanium, vanadium and silicon.

Thus, the invention relates to a method for obtaining acrolein from glycerol or glycerine, in the presence of a catalyst as defined above, and to the use of this catalyst for converting glycerol or glycerine into acrolein. A catalyst of the invention allows controlled conversion of glycerol or glycerine into acrolein, i.e. not promoting conversion as far as acrylic acid. For this purpose, a preferred catalyst of the invention does not comprise, or does not comprise in a majority weight proportion relatively to each of the other oxides making it up, of molybdenum oxide and/or copper oxide.

This is why the invention also relates to the use of at least any one of the catalysts a), b), c), d), e) and f), as defined earlier for converting glycerol or glycerine into acrolein.

The catalyst may be prepared in various ways (co-precipitation, hydrothermal synthesis . . . ). An effective procedure was described by Kantcheva et.al., Catalysis Communications (2008), 9(5), p 874-879, in patents FR 2907444 and FR 2907445.

The catalyst defined earlier may further meet the preferential characteristics below considered alone or as a combination:
- the catalysts a)-f) only comprise the oxides and mixed oxides defined earlier,
- at least one of the oxides, either mixed or not, of said catalysts a)-f) is supported,
- the molar ratio Zr/some of the other constitutive elements of said catalysts a)-f) different from Zr, i.e. selected from Si, Ti and M, varies from 0.5 to 200, more advantageously it varies from 1 to 100.

As stated earlier, the catalyst of the invention has the benefit of being able to be easily regenerated, and this without affecting the yield of the dehydration or the acrolein selectivity.

The reaction according to the invention may be applied in a gas phase or in a liquid phase, preferably in a gas phase.

When the reaction is conducted in a gas phase, different process technologies may be used, i.e. a fixed bed process, a fluidized bed process or a process with a circulating fluidized bed. In the first two processes, in a fixed bed or in a fluidized bed, the regeneration of the catalyst may be separated from the catalytic reaction. For example it may be accomplished ex situ with conventional regeneration methods, such as combustion in air or with a gas mixture containing molecular oxygen. According to the method of the invention, the regeneration may be accomplished in situ since the temperatures and pressures at which regeneration is accomplished are close to the reaction conditions of the process.

Regarding the liquid phase process, the reaction may be achieved in a conventional reactor for reaction in a liquid phase on a solid catalyst, but also in a reactor of the catalytic distillation type considering the significant difference between the boiling points of glycerol (290° C.) and of acrolein (53° C.). A process in a liquid phase may also reasonably be contemplated at a relatively low temperature which allows continuous distillation of the produced acrolein, thereby limiting the consecutive reactions of acrolein degradation. The experimental conditions of the reaction in the gas phase are preferably a temperature comprised between 250 and 400° C., at a pressure comprised between 1 and 10 bars. In the liquid phase, the reaction operates between 150 and 350° C. and at a pressure which may range from 3 to 70 bars.

Another advantage of the method of the invention lies in the form of the starting glycerol or glycerine which may be in pure or partly purified form or in solution, notably an aqueous solution. Advantageously, an aqueous solution of glycerol is used. In an aqueous solution, the concentration of the glycerol is preferably of at least 1%, at best it varies from 10 to 50% by weight and preferably between 15 and 30% by weight in the reactor. The glycerol concentration should not be too high for the purpose of avoiding parasitic reactions which burden the acrolein yield, like the formation of glycerol ethers or acetalization reactions between the produced acrolein and the non-converted glycerol. Moreover, the glycerol solution should not be too diluted, because of a redhibitory energy cost induced by the evaporation of the glycerol. In every case, it is easy to adjust the glycerol concentration of the solution by partly or totally recycling the water produced by the relevant reaction. Energy optimization at the bounds of the synthesis tends to recover heat at the reaction output in order to vaporize the flow of glycerol supplied to the reactor.

The invention further provides a method for making 3-(methylthio)propionic aldehyde (MMP), 2-hydroxy-4-methylthiobutyronitrile (HMTBN), methionine, 2-hydroxy-4-methylthiobutanoic acid (HMTBA), esters of the latter, notably the isopropyl ester, and 2-oxo-4-methylthiobutanoic acid (KMB) from acrolein, according to which the acrolein is obtained by a method described above. Comparatively to the conventional method for making acrolein by controlled oxidation of propylene, the acrolein produced according to the aforementioned method may contain impurities different from those of the traditional method, both under the angle of their amount and of their nature. According to the contemplated use, synthesis of acrylic acid or of methionine or its hydroxyl analog, purification of acrolein may be contemplated according to techniques known to one skilled in the art.

Thus, once the acrolein is directly obtained according to the invention or after purification, it is set to react with methylmercaptan (MSH) in order to produce 3-(methylthio) propionic aldehyde (or MMP). In a following step, the MMP is put into contact with hydrocyanic acid in order to produce 2-hydroxy-4-(methylthio)butryronitrile (HMTBN). After synthesis of HMTBN, various reaction steps lead to methionine, its hydroxyl analog (HMTBA), the esters of the latter or its oxo analogue (KMB). All these steps from the synthesis of acrolein are well known to one skilled in the art.

BRIEF DESCRIPTION OF THE DRAWINGS

The present invention is now described in more detail and illustrated with the examples and figures hereafter without however limiting the scope thereof.

FIG. 1 shows the development of the conversion into glycerol and of the corresponding acrolein selectivity over time, on each of the catalysts A, B, C and D described in the examples 1, 7, 8 and 9 respectively; the catalysts A and B are catalysts of the invention, the catalysts C and D are catalysts of the prior art. The time indicated for each point is that of the end of sampling corresponding to trapping for one hour. The reaction conditions and the calculation methods used by the acrolein conversion and selectivity are described later on.

This figure is read, substantiated by the following caption:
conversion into glycerol on catalyst A (□), B (Δ), C (◇) or D (○)
acrolein selectivity on catalyst A (■), B (▲), C (♦) or D (●)

This figure is read, substantiated by the following caption.
conversion into glycerol with fresh catalyst (Δ) and with regenerated catalyst (▲)
acrolein selectivity with fresh catalyst (□) and with regenerated catalyst (■)

This figure is read substantiated by the following caption:
conversion into glycerol with catalyst A' (♦), D (●) or C (Δ)
acrolein selectivity with catalyst A' (■), D (×) or C (▲)

This figure is read substantiated by the following caption:
conversion into glycerol with a fresh catalyst (Δ) and with a regenerated catalyst (▲)
acrolein selectivity with a fresh catalyst (□) and with a regenerated catalyst (■).

DETAILED DESCRIPTION

The reaction conditions and the methods for calculating the conversion and acrolein selectivity are described hereafter.

The reaction for dehydration of the glycerol is conducted on the indicated catalysts, at atmospheric pressure, in a straight reactor with a fixed bed of diameter 18 mm. The reactor is placed in an oven which allows the catalyst to be maintained at the reaction temperature which is 300° C. The volume of catalyst loaded into the reactor is 4.5 mL, which gives a bed height of about 1.8 cm. The reactor is fed with a flow rate of 3.77 g/h of aqueous solution with 20% by weight of glycerol. The aqueous solution is vaporized by means of a C.E.M (Controlled Evaporator Mixer) Bronkhorst® evaporator in the presence of a nitrogen flow rate of 75 mL/min. The glycerol/water/nitrogen molar relative portion is 2.3/46.3/51.4. The calculated contact time is of the order of 1.9 s i.e. a GHSV of 1930 h$^{-1}$. The contact time is defined as follows:

Contact time=catalyst volume×$P_{atm}$/(total molar flow rate×Temperature×$R$)

with $P_{atm}$=101,325 Pa, Temperature=25° C. and total molar flow rate=molar flow rate of glycerol+molar flow rate of water+molar flow rate of the inert gas.

After reaction, the products are condensed, two systems of condensations were used. Examples 10, 11, 12, 16, 17 and 18 were obtained with a system of three traps mounted in series. The first trap contains a known mass of water and is cooled by crushed ice. The two other traps contain ethanol and are cooled by a cryostat to −25° C. Examples 13, 14 and 15 were obtained with a simple trap containing a known mass of water and cooled by crushed ice. The trapping period is one hour and the feed rate is not interrupted during the changes of traps.

The formed products are analyzed by chromatography, two analyses are conducted for each sample:

The main products of the reaction are analyzed by gas chromatography on a capillary column (Nukol, 30 m×0.53 mm) with a Shimadzu 2014 chromatograph provided with an FID detector. The quantified products during this analysis are: acrolein, acetaldehyde, acetone, propionaldehyde, hydroxypropanone, acetic acid, allyl alcohol and phenol;

The remaining glycerol is quantified by gas chromatography with a Hewlett Packard chromatograph equipped with an FID detector and a capillary column (Carbowax or ZBwax, 30 m×0.32 mm).

The glycerol conversion, the acrolein selectivity and the yield of different products are defined as follows:

Glycerol conversion (%)=100×(1−number of remaining glycerol moles/number of introduced glycerol moles)

Acrolein selectivity (%)=100×(number of produced acrolein moles/number of unreacted glycerol moles)

Yield of $X$ (%)=$K$×100×number of produced $X$ moles/number of introduced glycerol moles With K=1 if X is acrolein, acetone, hydroxypropanone, propanol or allyl alcohol; K=⅔ if X=acetaldehyde or acetic acid and K=2 if X=phenol.

EXAMPLE 1

Preparation and Characterization of the Catalyst A

A catalyst according to the invention of the zirconium and niobium oxide type prepared from zirconium oxide hydrate and ammonium oxalate-niobiate, $(NH_4)(C_2O_4)_2NbO.xH_2O$ (Aldrich, 99.99%). The zirconium oxide hydrate is prepared by co-precipitation of a solution of zirconium oxonitrate $ZrO(NO_3)_2.xH_2O$ (Aldrich, 99%) and a 28% ammonia solution at pH=8.8.

The ammonium oxalate-niobiate is dissolved in permuted water acidified with concentrated HNO$_3$ at pH∼0.5 and heated to 45° C. After returning to room temperature, the zirconium hydroxide hydrate is added in a $ZrO_2/Nb_2O_5$ molar ratio of 3:1, the hydration degree of the zirconium oxide hydrate is determined beforehand by thermogravimetric analysis (TGA). After 24 h with stirring, the mixture is filtered and the solid is calcined under air flow at 600° C. The specific surface area of this catalyst is 40 m$^2$/g. The specific surface areas of the solids were measured with the BET (Brunauer Emmet and Teller) method at −196° C. on a Micromeritics ASAP 2020 apparatus. The solids are desorbed beforehand at 300° C. for 3 h in a vacuum of 5×10$^{-5}$ mbars. The niobium and zirconia contents of the different prepared solids were determined by ICP-OES (Inductively Coupled Plasma Optical Emission Spectrometry). The Zr/Nb molar ratio of the catalyst A calculated from these analyses is 9.3.

EXAMPLE 2

Preparation and Characterization of the Catalyst A'

A catalyst according to the invention of the zirconium and niobium oxide type is prepared according to the procedure described by Kantcheva. et. Al, Catalysis Communications (2009), 9(5), p 874-879, by impregnation of zirconium oxide hydrate.

The zirconium oxide hydrate was prepared by co-precipitation of a solution of zirconium oxonitrate $ZrO(NO_3)_2.xH_2O$ (Aldrich, 99%) and of a 28% ammonia solution. The precursor of Nb(V), $(NH_4)(C_2O_4)_2NbO.xH_2O$ (Aldrich, 99.99%) is added with stirring to a 35% hydrogen peroxide solution (Sigma Aldrich) acidified to pH≈0.5 with concentrated HNO$_3$ and heated to 50° C. The H$_2$O$_2$/oxalate molar ratio is 13/1. The solution is heated for 1h at 50° C. before being cooled down to room temperature. Next, the zirconium oxide hydrate is again added while ensuring a $ZrO_2Nb_2O_5$ ratio of 6:1, the hydration degree of the zirconium oxide hydrate being determined by thermogravimetric analysis (TGA). The mixture is left with stirring at room temperature for 24 hrs and the liquid phase is then evaporated in vacuo at T<70° C. The obtained solid is calcined under air flow at 600° C.

The specific surface area of this catalyst is 51 m$^2$/g. The specific surface areas of the solids were measured by the BET (Brunauer Emmet and Teller) a −196° C. on a Micromeritics ASAP 2020 apparatus. The solids are desorbed beforehand at 300° C. for 3 hours in a vacuum of 5×10$^{-5}$ mbars. The niobium and zirconium contents of the obtained solids were determined by ICP-OES. The Zr/Nb molar ratio of this solid is 3.3.

EXAMPLE 3

Preparation and Characterization of the Catalyst E

A catalyst according to the invention of the zirconium and niobium oxide type is prepared according to the procedure described by Kantcheva. et. Al, (Catalysis Communications 9(5), (2008) p 874-879), by impregnation of zirconium oxide hydrate with a solution containing a mixed ammonium and niobium oxalate.

The precursor of Nb(V), $(NH_4)(C_2O_4)_2NbO.xH_2O$ (Aldrich, 99.99%) is added with stirring to a 35% hydrogen peroxide solution (Sigma Aldrich) acidified to pH∼0.5 with concentrated HNO$_3$ and heated to 50° C. The H$_2$O$_2$/oxalate molar ratio is 13/1. The solution is heated for 1 h at 50° C. before being cooled down to room temperature. Next, the zirconium oxide hydrate prepared beforehand by co-precipitation of a solution of zirconium oxonitrate (ZrO (NO$_3$)$_5$.xH$_2$O (Aldrich, 99%) and of a 28% ammonia solution, is added while ensuring a ZrO$_2$:Nb$_2$O$_5$ ratio of 6:1. The mixture is maintained with stirring at room temperature for 24 hrs and the liquid phase is then evaporated in vacuo at T<70° C. The obtained solid is calcined under an air flow at 600° C.

The specific surface area of this catalyst determined in a similar way to that of catalyst A is 39 m$^2$/g. The niobium and zirconium contents of the obtained solid were determined by ICP-OES. The molar ratio Zr/Nb of this solid is 3.7.

EXAMPLE 4

Preparation and Characterization of the Catalyst F

A catalyst according to the invention of the zirconium, niobium and vanadium oxide type is prepared. The vanadium precursor was prepared from NH$_4$VO$_3$ (Sigma, ACS Reagent 99.7%) according to the following method:

Ammonium metavanadate is dissolved in a 9% hydrogen peroxide solution containing oxalic acid (Aldrich, 99%). The oxalic acid/introduced NH$_4$VO$_3$ molar ratio is 1.3. After 1 hr with stirring at room temperature, the solution is evaporated in vacuo; a blue solid is obtained. The vanadium oxide content of this compound is determined by thermogravimetric analysis.

The vanadium precursor, the mixed niobium and ammonium oxylate (NH$_4$)C$_2$O$_4$)2NbO.xH$_2$O (Aldrich, 99.99%), and the zirconium oxide hydrate prepared as described in Example 1 are introduced into an aqueous solution acidified with concentrated HNO$_3$ (pH<0.5) with a Zr/Nb/V molar ratio of 72/22/3.2. After 24 hrs with stirring, the reaction medium is filtered and the solid is calcined under air flow at 600° C. The specific surface area of this catalyst determined in a similar way to that of catalyst A is 48 m$^2$/g. The niobium, vanadium and zirconium contents of the obtained solid were determined by ICP-OES. The Zr/Nb/V molar composition of this catalyst is 90.4/8.4/1.2.

EXAMPLE 5

Preparation and Characterization of the Catalyst G

A catalyst according to the invention of the tungstated zirconia type doped with silica is prepared. The preparation of this solid includes three steps. The first step is the synthesis of zirconium hydroxide hydrate by co-precipitation of a solution of zirconium oxonitrate ZrO(NO$_3$)$_2$.xH$_2$O (Aldrich, 99%) and a 29% ammonia solution at pH=8.8. The second step comprises stabilizing the zirconium hydroxide hydrate with silicic species according to the procedure described by Nahas et.al (Journal of Catalysis 247 (2007), p 51-60). The zirconium hydroxide hydrate is placed in a glass flask containing an ammoniacal solution, the pH of which is adjusted to 11. The mixture is refluxed for 72 hrs and then filtered and washed with permuted water. The last step is the exchange between tungstic acid H$_2$WO$_4$ (Aldrich 99%) dissolved in hydrogen peroxide and zirconium hydroxide. The tungstic acid is dissolved in a 35% hydrogen peroxide solution at 60° C. The tungstic acid concentration of the solution is 0.04M. The tungstic acid solution is then cooled down to room temperature, and the zirconium hydroxide doped with silica is slowly added. The obtained solid is filtered and then calcined in air at 650° C. Its specific surface area is 40 m$^2$/g. The niobium, silicon and zirconium contents of the solid were determined by ICP-OES. The W/Si/Zr molar composition of this catalyst is 4.7/1.4/93.9.

EXAMPLE 6

Synthesis of the Catalyst H

The catalyst H is prepared according to the synthesis method described in Example 1. The pH of the nitric acid solution is slightly more acid (pH<0.1) in the case of the catalyst H. The obtained solid has a specific surface area of 57 m$^2$/g and a Zr/Nb molar ratio of 11.8.

EXAMPLE 7

Preparation and Characterization of the Catalyst B

The ZrTiSiW catalyst according to the invention was prepared by Rhodia according to the method described in patent FR2907445A. The specific surface area of this catalyst, determined in a similar way to that of catalyst A, is 105 m$^2$/g. The weight composition of oxides of this catalyst is 54% of ZrO$_2$, 35% of TiO$_2$, 7.5% of SiO$_2$ and 3.5% of WO$_3$.

EXAMPLE 8

Preparation and Characterization of the Catalyst C (A Comparative Catalyst from the Prior Art)

The catalyst C is a tungstated zirconia (89.5% ZrO$_2$-10.5% WO$_3$) synthesised by Daiichi Kigenso (supplier reference: Z-1104). The specific surface area of this catalyst determined in a similar way to that of catalyst A is 77 m$^2$/g.

EXAMPLE 9

Preparation and Characterization of the Catalyst D (A Comparative Catalyst from the Prior Art)

Catalyst D is an H-ZSM-5 zeolite provided by Zeochem (ZEOcat PZ-2/5OH). The specific surface area of this catalyst determined in a similar way to that of catalyst A is 406 m$^2$/g.

EXAMPLE 10

Catalytic Dehydration of Glycerol into Acrolein: Evaluation of the Catalysts A, B, C and D Table 1 gives the performances obtained with the catalysts A, B, C and D at 6 hrs of reaction.

TABLE 1

|  | A (invention) | B (invention) | C (comparative) | D (comparative) |
|---|---|---|---|---|
| Conversion of glycerol | 100 | 100 | 94 | 57 |
| Acrolein selectivity | 66 | 69 | 64 | 65 |
| Acrolein yield | 66 | 69 | 60 | 37 |
| Acetaldehyde yield | 6.3 | 6.5 | 3.9 | 0.6 |
| Propionaldehyde yield | 3.1 | 5.4 | 2.8 | 1.6 |
| Acetone yield | 1.7 | 2.7 | 1.6 | 0.0 |
| Allyl alcohol | 0.1 | 0.5 | 0.5 | 0.2 |
| Hydroxypropanone yield | 5.8 | 3.1 | 6.1 | 3.0 |
| Phenol yield | 2.6 | 0.8 | 0.3 | — |

This table shows that with an equal catalyst volume, only the catalysts A and B (according to the invention) allow total conversion of the glycerol. Further, with the catalysts of the invention, it is possible to obtain better acrolein selectivity, already visible at 6 hrs and which is confirmed at 50 hrs, with an acrolein yield of 70% for catalyst A and 80% for catalyst B.

The catalysts A and B are therefore more active and more selective than the catalysts of the prior art.

EXAMPLE 11

Figure 1:
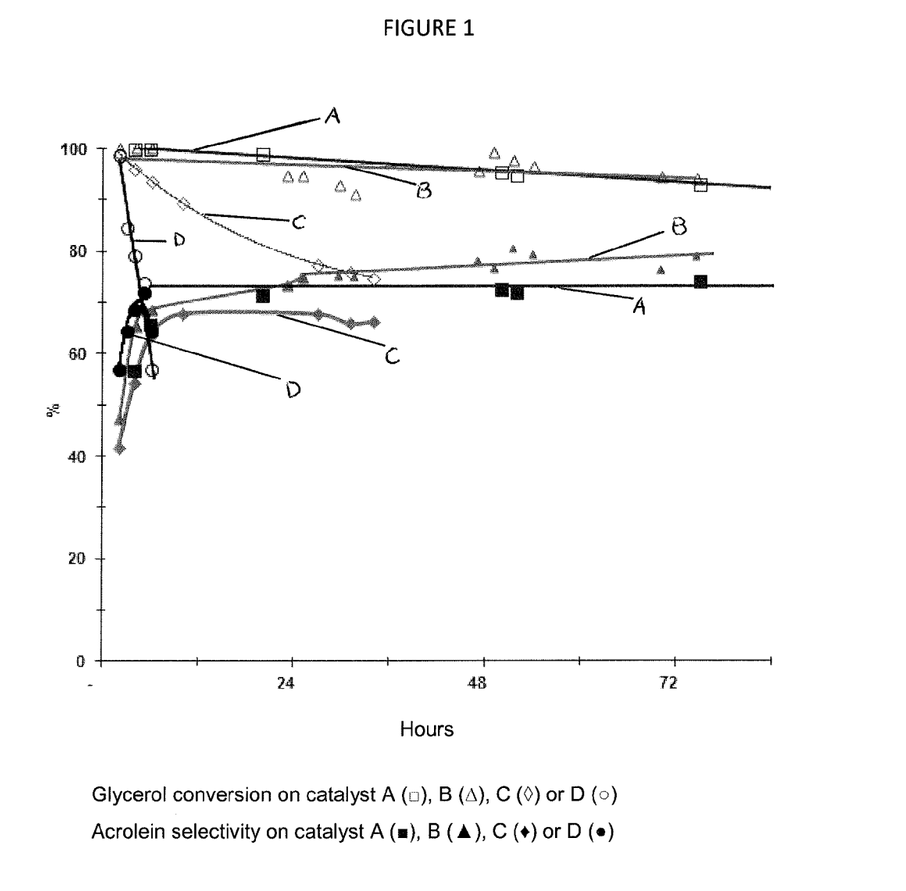

Catalytic Dehydration of Glycerol into Acrolein: Time-Dependent Change of the Performances of the Catalysts A, B, C and D The change in the performances of the catalyst A, B, C and D over time, obtained under the same conditions as in Example 4 is shown in FIG. 1.

The catalysts A and B (invention) maintain constant acrolein selectivity and high glycerol conversion over several days unlike the catalysts C and D of the prior art which are strongly deactivated within less than 24 hrs.

The catalysts A and B of the invention are therefore more active, more acrolein-selective but also more stable over time than the best catalysts claimed in the prior art.

EXAMPLE 12

Regeneration of the Catalyst A

After 143 hrs in a reaction mixture at 300° C., the catalyst A according to the invention is regenerated under an air flow of 450° C. for 2 hrs (air flow rate: 51 mL/min). After regeneration, the catalyst is tested under the same operating conditions as before regeneration.

Figure 2:
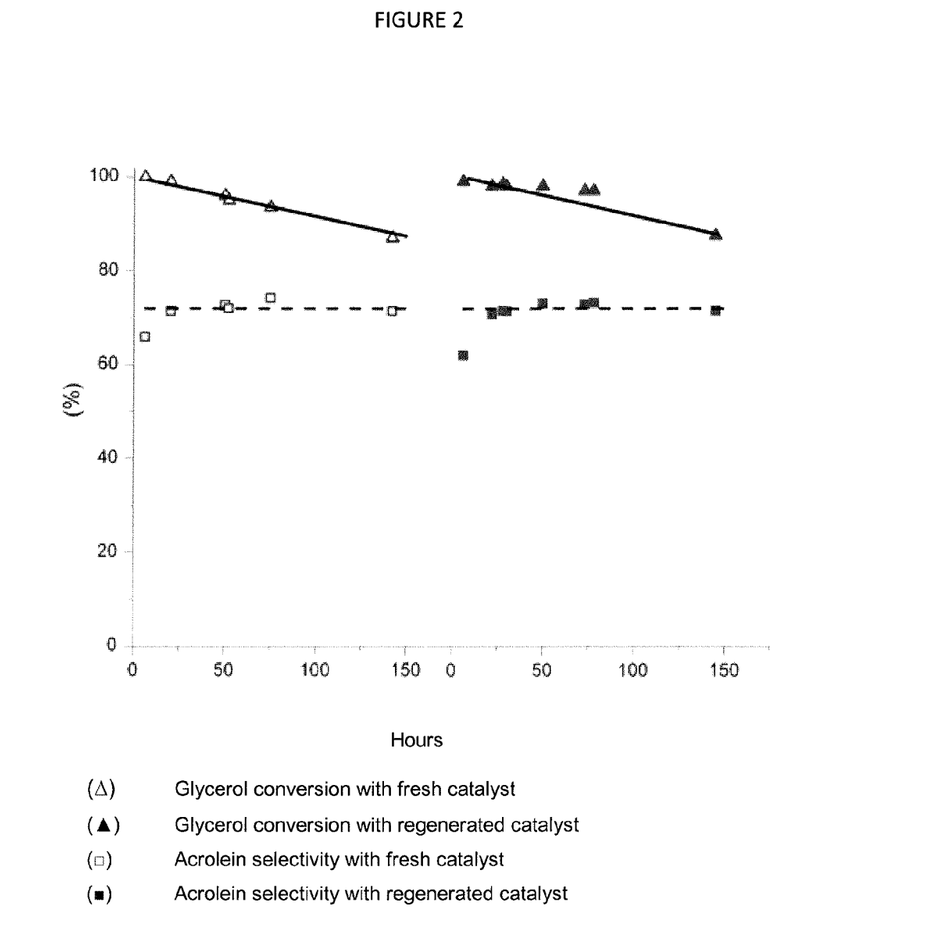
FIG. 2 illustrates the conversion to glycerol and the acrolein selectivity obtained on the catalyst A according to the invention before and after regeneration under an air flow.

The obtained results are shown in FIG. 2. The regeneration in air at 450° C. allowed the catalyst A to recover its activity and its initial yield. The catalyst A according to the invention is therefore regenerable over a short time and without any loss of activity and selectivity. Not only the catalyst A is active and selective but it is also entirely and easily regenerable.

EXAMPLE 13

Catalytic Dehydration of Glycerol into Acrolein: Comparison of the Catalytic Properties of the Catalysts A', D and C Table 2 gives the performances obtained at 300° C. with the catalysts A', B and C at 5 hrs of reaction.

TABLE 2

|  | A' (invention) | D (comparative) | C (comparative) |
|---|---|---|---|
| Glycerol conversion | 100 | 88 | 99 |
| Acrolein yield | 46.8 | 38.8 | 45.6 |
| Acrolein selectivity | 47 | 44 | 46 |
| Acetaldehyde yield | 7.9 | 1.3 | 4.6 |
| Propionaldehyde yield | 14.3 | 3.5 | 8.9 |
| Acetone yield | 1.4 | 0 | 2.1 |
| Allyl alcohol yield | 0.9 | 0.5 | 0.5 |
| Hydroxypropanone yield | 3.4 | 4.8 | 5.8 |
| Acetic acid yield | — | 0.9 | 0.6 |
| Phenol yield | 3.4 | 0.2 | 1.3 |

This table shows that with an equal volume of catalysts, only catalyst A' (according to the invention) allows total conversion of the glycerol. Further, with the catalyst A', it is possible to obtain better acrolein selectivity. The catalyst A' is therefore more active and more selective than the catalysts of the prior art.

EXAMPLE 14

Catalytic Dehydration of Glycerol into Acrolein: Time-Dependent Change in the Performances of the Catalysts A', D and C.

Figure 3:
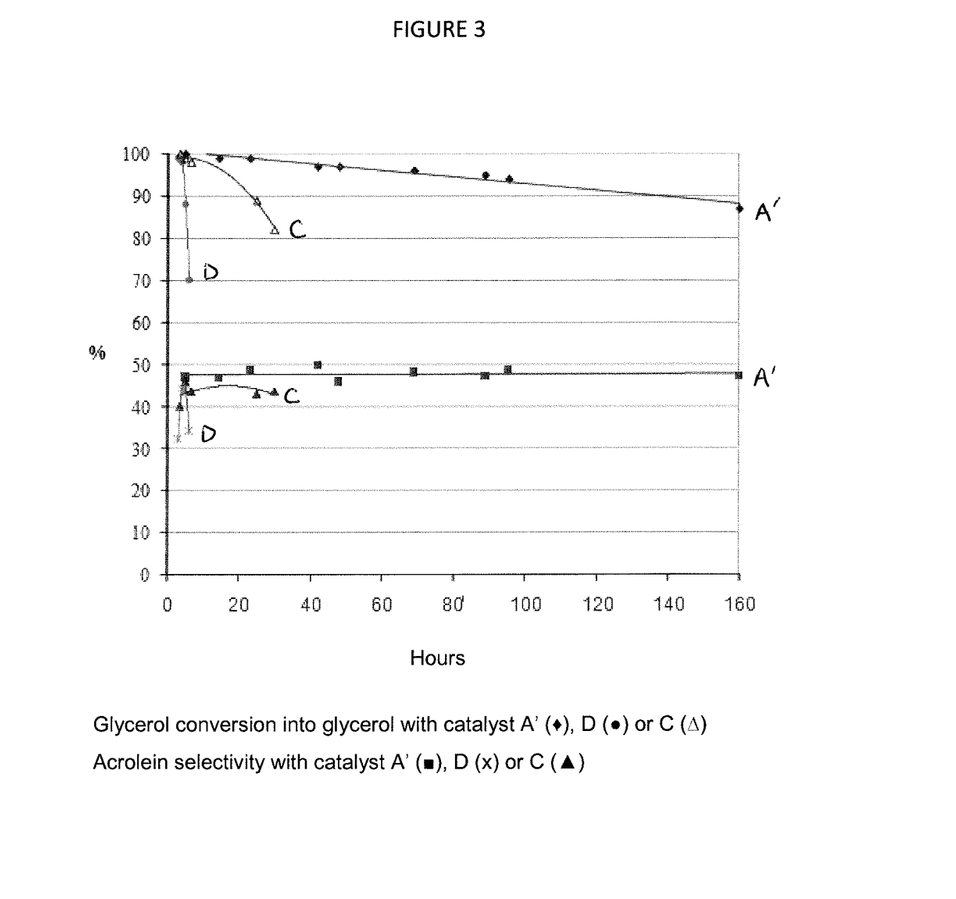
FIG. 3 illustrates a comparison of the conversion into glycerol and of the acrolein selectivity of this conversion over time, with each of the catalysts A', C and D described in Examples 2, 8 and 9 respectively; catalyst A' is a catalyst of the invention, catalysts C and D are catalysts of the prior art.

The change in the performances of the catalysts A', D and C over time is shown in FIG. 3.

The catalyst A' (invention) maintains quasi-constant acrolein selectivity and high glycerol conversion over one week in a reaction flow unlike the catalysts D and C of the prior art which are strongly deactivated within less than 24 hrs.

The catalyst A' of the invention is therefore more active, more acrolein selective and more stable over time than the best catalysts claimed in the prior art.

EXAMPLE 15

Regeneration of Catalyst A'

After 183 hrs in a reaction mixture, the catalyst A' according to the invention is regenerated under air flow at 450° C. for 1 hr (air flow rate: 51 mL/min). After regeneration, the catalyst is tested under the same operating conditions as before the regeneration.

Figure 4:
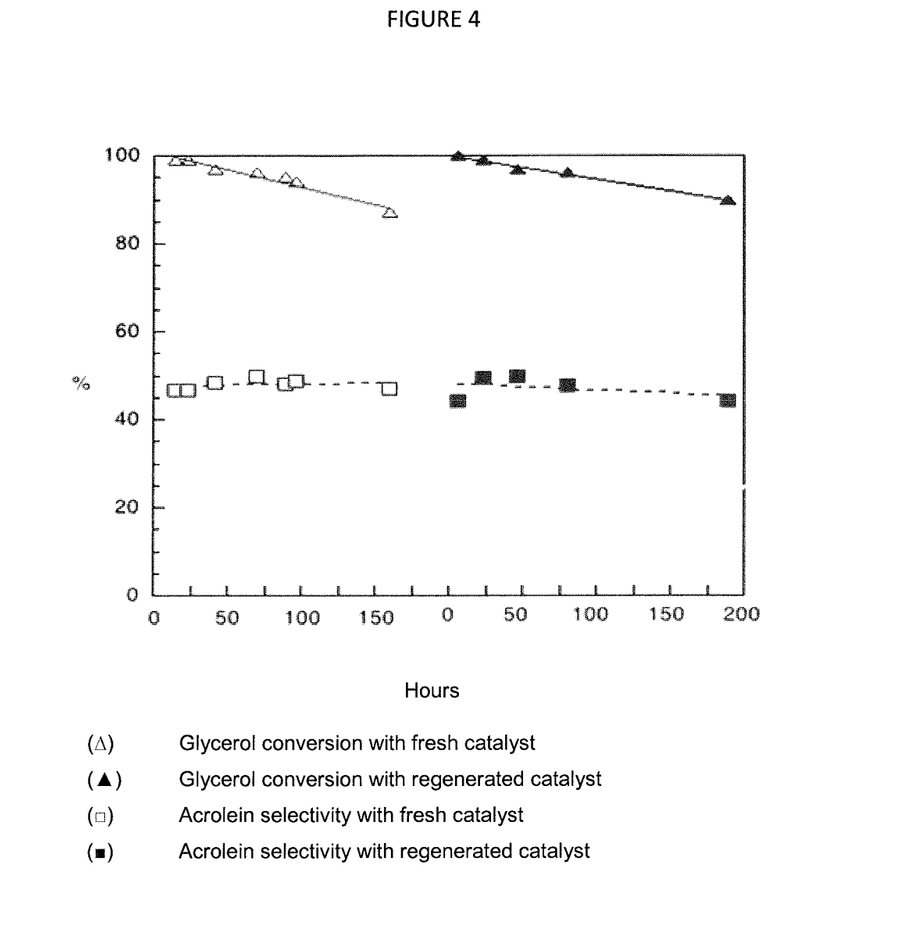
FIG. 4 illustrates the conversion into glycerol and the acrolein selectivity obtained with the catalyst A' according to the invention before and after regeneration under air flow.

The obtained results are shown in FIG. 4.

Regeneration in air at 450° C. allowed the catalyst A' to recover its activity and its initial yield. The catalyst A' according to the invention is therefore regenerable over a short time and without any loss of activity and selectivity. Not only the catalyst A' is active and selective but it is also entirely and easily regenerable.

EXAMPLE 16

Catalytic Dehydration of Glycerol into Acrolein: Evaluation of the Catalysts E and F (According to the Invention)

Table 3 gives the obtained performances of the catalysts E and F.

TABLE 3

|  | E | | | | | F | |
|---|---|---|---|---|---|---|---|
|  | Hour at the end of the sampling | | | | | | |
|  | 5 | 20 | 48 | 72 | 95 | 6 | 24 |
| Glycerol conversion | 100 | 98 | 97 | 94 | 90 | 100 | 94 |
| Acrolein selectivity | 60 | 72 | 73 | 72 | 71 | 50 | 51 |
| Acrolein yield | 60 | 71 | 71 | 68 | 63 | 50 | 48 |
| Actetaldehyde yield | 4.9 | 3.1 | 2.6 | 2.6 | 2.5 | 8 | 5.5 |
| Propionaldehyde yield | 6.8 | 4.8 | 3.9 | 3.9 | 3.8 | 5.8 | 4 |
| Acetone yield | 1.9 | 1.7 | 1 | 1.1 | 0.9 | 4.1 | 3.2 |
| Allyl alcohol yield | 0.6 | 0.7 | 0.7 | 0.7 | 0.7 | 3.2 | 4.4 |
| Hydroxypropanone yield | 5.1 | 12.2 | 13.5 | 13.1 | 12.4 | 3.1 | 7.7 |
| Phenol yield | 1.9 | 0.9 | 0.5 | 0.5 | 0.3 | 1.3 | 0.7 |

EXAMPLE 17

Catalytic Dehydration of Glycerol into Acrolein: Evaluation of the Catalyst G (According to the Invention)

Table 4 gives the performances of the catalyst.

TABLE 4

| Hour at the end of the sampling | 4 | 23 | 42 |
|---|---|---|---|
| Glycerol conversion | 98 | 96 | 87 |
| Acrolein selectivity | 68 | 80 | 83 |
| Acrolein yield | 67 | 77 | 72 |
| Actetaldehyde yield | 4.2 | 3.5 | 2.4 |
| Propionaldehyde yield | 3.1 | 2.4 | 1.6 |
| Acetone yield | 1.2 | 1.3 | 0.9 |
| Allyl alcohol yield | 0.7 | 0.9 | 0.6 |
| Hydroxypropanone yield | 5.2 | 10.9 | 9.7 |
| Phenol yield | 0.8 | 0.2 | — |

EXAMPLE 18

Obtaining Acrolein from Non-pure Glycerol with the Catalyst H

The performances of catalyst H were evaluated with a solution of raw industrial glycerine with a titer of 82% by weight. This glycerine is characterized in that it contains more than 15% by weight of methanol. As in the previous examples, the catalyst volume in the reactor is 4.5 mL, the nitrogen flow rate is 74.5 mL/min and the reaction temperature is 300° C. The flow rate of the aqueous solution with 20% by weight of glycerine is 3.77 g/h. The glycerol/water/nitrogen molar relative proportion is 1.9/46.5/51.6. The obtained results are given in table 5.

TABLE 5

| | Hour at the end of the sampling | | | | | |
|---|---|---|---|---|---|---|
| | 8 | 26 | 51 | 76 | 100 | 172 |
| Glycerol conversion | 100 | 100 | 100 | 100 | 99 | 90 |
| Acrolein selectivity | 56 | 71 | 73 | 73 | 73 | 75 |
| Acrolein yield | 56 | 71 | 73 | 73 | 72 | 68 |
| Actetaldehyde yield | 7.4 | 6.2 | 5.4 | 4.6 | 3.9 | 2.8 |
| Propionaldehyde yield | 5.2 | 3.6 | 3.1 | 2.8 | 2.4 | 1.9 |
| Acetone yield | 2.0 | 2.0 | 1.4 | 1.2 | 0.9 | 0.6 |
| Allyl alcohol yield | 0.9 | 1.3 | 1.4 | 1.5 | 1.5 | 1.5 |
| Hydroxypropanone yield | 1.9 | 11.1 | 14.5 | 15.6 | 17.9 | 17.5 |
| Phenol yield | 5.0 | 1.7 | 0.9 | 0.6 | 0.4 | 0.2 |

The presence of a significant amount of methanol does not lower the performances of the catalyst of the invention.

The invention claimed is:

1. A method for preparing acrolein from glycerol or glycerine, where dehydration of the glycerol or glycerine is achieved in the presence of a catalyst based on zirconium oxide, the catalyst comprising:
   (a) a mixed oxide of zirconium and of at least one metal M, said metal being selected from niobium, tantalum and vanadium, or
   (b) a zirconium oxide and at least one metal M oxide, said metal being selected from niobium, tantalum and vanadium, or
   (c) a silicon oxide, a mixed oxide of zirconium and of at least two metals M, said metals being selected from tungsten, cerium, manganese, niobium, tantalum, titanium, and vanadium, or
   (d) a titanium oxide, a mixed oxide of zirconium and of at least one metal M, said metal being selected from tungsten, cerium, manganese, niobium, tantalum, titanium, vanadium and silicon, and
   wherein all of said oxides are obtained by calcination.

2. The method according to claim 1, wherein at least one of the oxides of said catalyst (a), (b), (c) and (d) is supported.

3. The method according to claim 1, wherein the glycerol is in aqueous solution at a concentration of at least 1% by weight.

4. The method according to claim 3, wherein the glycerol concentration of the aqueous solution varies from 10 to 50% by weight.

5. The method according to claim 1, wherein the catalyst is regenerated.

6. The method according to claim 1, wherein the dehydration reaction is conducted in a gas phase.

7. The method according to claim 6, wherein the dehydration reaction is conducted in a reactor with a fixed bed, a fluidized bed, or a circulating fluidized bed.

8. The method according to claim 1, wherein the dehydration reaction is conducted in a liquid phase.

9. The method according to claim 1, wherein the catalyst comprises a silicon dioxide and a mixed oxide of zirconium and at least tungsten.

10. A method of preparing acrolein from glycerol or glycerine comprising
   dehydration of glycerol or glycerin in the presence of a catalyst based on zirconium oxide,
   wherein the catalyst comprises a mixed oxide of zirconium and niobium, and
   wherein the dehydration step comprises contacting a stream consisting of glycerol, water, and nitrogen with the catalyst.

11. The method according to claim 1, wherein calcination is carried out at a temperature of 600-650° C.

12. The method according to claim 1, wherein the catalyst comprises at least
   (a) a mixed oxide of zirconium and of at least niobium and
   (b) a zirconium oxide and at least one metal M oxide, said metal being selected from the group consisting of niobium, tantalum, and vanadium.

13. The method according to claim 1, wherein the (Zr/sum of the elements Si, Ti and Nb) molar ratio varies from 0.5 to 200.

14. The method according to claim 13, wherein said molar ratio varies from 1 to 100.

* * * * *